(12) United States Patent
Al Shail et al.

(10) Patent No.: US 9,981,118 B2
(45) Date of Patent: May 29, 2018

(54) IMPLANTABLE COUPLING ASSEMBLY FOR A CATHETER TUBE AND A VALVE DEVICE

(71) Applicant: King Faisal Specialist Hospital & Research Centre, Riyadh (SA)

(72) Inventors: Essam Al Shail, Riyadh (SA); Falah Redha, Bern (CH)

(73) Assignee: King Faisal Specialist Hospital and Research Center, Riyadh (SA)

( * ) Notice: Subject to any disclaimer, the term of this patent is extended or adjusted under 35 U.S.C. 154(b) by 119 days.

(21) Appl. No.: 14/596,502

(22) Filed: Jan. 14, 2015

(65) Prior Publication Data

US 2015/0196748 A1    Jul. 16, 2015

Related U.S. Application Data

(60) Provisional application No. 61/927,305, filed on Jan. 14, 2014.

(51) Int. Cl.
*A61M 39/10* (2006.01)
*A61M 39/12* (2006.01)

(52) U.S. Cl.
CPC .......... *A61M 39/10* (2013.01); *A61M 39/12* (2013.01); *A61M 2039/1027* (2013.01); *A61M 2039/1066* (2013.01); *Y10T 29/4987* (2015.01)

(58) Field of Classification Search
CPC ............. A61M 39/10; A61M 39/1011; A61M 39/105; A61M 39/1055; A61M 39/12; A61M 39/14; A61M 2039/1005; A61M 2039/1016; A61M 2039/1027; A61M 39/1033; A61M 39/1044; A61M 39/1061; A61M 2039/1066; A61M 2039/1094
See application file for complete search history.

(56) References Cited

U.S. PATENT DOCUMENTS

| 3,876,234 | A | * | 4/1975 | Harms | A61M 39/10 |
| | | | | | 285/332 |
| 4,895,570 | A | * | 1/1990 | Larkin | A61M 39/1011 |
| | | | | | 604/411 |
| 7,370,889 | B2 | * | 5/2008 | Maunder | F16L 33/225 |
| | | | | | 285/148.17 |
| 7,722,090 | B2 | * | 5/2010 | Burton | A61M 39/10 |
| | | | | | 285/332 |
| 2006/0161115 | A1 | * | 7/2006 | Fangrow | A61M 39/26 |
| | | | | | 604/249 |

(Continued)

*Primary Examiner* — Bhisma Mehta
*Assistant Examiner* — James D Ponton
(74) *Attorney, Agent, or Firm* — Pearl Cohen Zedek Latzer Baratz LLP

(57) ABSTRACT

A coupling assembly for securing an end of a tube to a connecting shaft of a device is provided. The coupling assembly comprises an inner sleeve having a first end, an opposite second end, a first end section at the first end and a second end section at the second end, and an outer sleeve having a first end, an opposite second end and a second end section at the second end. The second end section of the outer sleeve is sized and shaped to receive at least the first end section of the inner sleeve therein. An interior surface of the second end section of the outer sleeve is provided with a protrusion or a recess to engage a corresponding recess or protrusion on an exterior surface of the inner sleeve. The second end section of the inner sleeve is flexible.

18 Claims, 8 Drawing Sheets

(56) References Cited

U.S. PATENT DOCUMENTS

2008/0004600 A1\* 1/2008 Kitani .................. A61M 39/10
  604/533
2012/0041426 A1\* 2/2012 Bizup ................ A61M 39/1011
  604/536

\* cited by examiner

IMPLANTABLE COUPLING ASSEMBLY FOR A CATHETER TUBE AND A VALVE DEVICE

CROSS REFERENCE TO RELATED APPLICATIONS

This application claims the benefit of U.S. Provisional Patent Application No. 61/927,305, filed Jan. 14, 2014, the entire contents of which are incorporated by reference.

BACKGROUND OF THE INVENTION

The present invention relates to a coupling assembly for securing a tube to a connector shaft of a device. In particular, the present invention relates to a coupling assembly for securing a catheter tube to a connector shaft of a device having a pump, a valve or a filter, that is implantable into a patient's body.

First identified in ancient Egyptian medical literature about 5000 years ago, hydrocephalus is a condition where normal flow of cerebrospinal fluid (CSF) produced in the ventricles is interrupted, either by obstruction or a failure of the body to re-absorb the CSF, causing intracranial pressure to increase. By some estimates, hydrocephalus may be the most prevalent neurological condition known to medical science, but exact numbers are hard to come by since no one keeps data on adults with hydrocephalus. If left untreated, symptoms will usually get worse over time, which can lead to permanent brain damage and event death.

The most common treatment for hydrocephalus is to surgically implant a shunt to drain the excess fluid to another part of the body where it can be absorbed, as illustrated in FIG. 1. If the patient is deemed a candidate, an endoscopic third ventriculostomy (ETV) can be performed, where a hole is made in the floor of the third ventricle to make a new path for the CSF to be absorbed by the body. Shunt surgery involves implanting a thin tube, called a shunt, in the brain. FIG. 1 shows a schematic 3D diagram of a patient with an implanted catheter tube 1. The catheter tube 1 is implanted such that one end of the tube 1 is located in the skull of the patient to receive excess cerebrospinal fluid (CSF) in the brain, and the opposite end of the tube is located in the patient's peritoneal cavity. The excess cerebrospinal fluid (CSF) in the brain runs through the tube 1 to the abdomen. From here, the fluid is absorbed e.g. into the blood stream. The shunt may have a valve inside it to control the flow of CSF and to ensure that it does not drain too quickly. Shunts can come in a variety of forms, but most of them consist of a valve housing connected to two catheters, namely a ventricular catheter and a distal catheter. One end of the ventricular catheter is placed in the brain and one end of the distal catheter is usually placed in the peritoneal cavity.

One of the most common causes of shunt failure is disconnection or fracture of the shunt. Disconnection may occur at any site of connection along the course of the tubing. This is usually related to improper technique, such as too lose or too tight ligature which leads to damage of the tube. Moreover, the suture ligature may puncture the skin of premature babies.

SUMMARY OF THE INVENTION

It is therefore an object of the present invention to provide a coupling assembly for securing an end of a tube to a connector shaft of a device in a reliable, long-lived manner, and which avoids damages to the tube, the device and surrounding material, such as tissue of a patient. This problem is solved by the coupling assembly, the kit and the method as claimed herein. Preferred embodiments are addressed in the depending claims.

In a first aspect, a coupling assembly is provided. The coupling assembly comprises an inner sleeve having a first end, an opposite second end, a first end section at the first end and a second end section at the second end, and an outer sleeve having a first end, an opposite second end and a second end section at the second end. The second end section of the outer sleeve is sized and shaped to receive at least the first end section of the inner sleeve therein. An interior surface of the second end section of the outer sleeve is provided with a protrusion or a recess to engage a corresponding recess or protrusion on an exterior surface of the inner sleeve. The second end section of the inner sleeve is flexible.

The coupling assembly comprises an inner sleeve and an outer sleeve, in which the outer sleeve engages the inner sleeve. In some embodiments, the coupling assembly consists of the inner sleeve and the outer sleeve, i.e. it does not comprise any other components. In use, an end section of the tube fitted on a connector shaft of a device may be positioned within the second end section of the inner sleeve of the coupling assembly. As the second end section of the inner sleeve is flexible, it may be elastically fitted on the end section of the tube fitted on the connector shaft. The end section of the tube is then clamped between the second end section of the inner sleeve and the connecting shaft. In the assembled state, the tube is thus secured to the connector shaft due to elastic force of the second end section of the inner sleeve. Moreover, by engaging the outer sleeve to the inner sleeve, the inner sleeve is further compressed onto the end section of the tube, resulting in an even more reliable and secure coupling between the tube and the connector shaft. To enhance this effect, the protrusion or recess on the exterior surface of the inner sleeve may be arranged on the second end portion of the inner sleeve, i.e. where the inner sleeve surrounds the end section of the tube and the connector shaft.

In use, the inner sleeve and the outer sleeve are arranged outside the fluid flow, such that there is no risk of corrosion or wear-out due to the fluid, or of contaminating or otherwise affecting the fluid through the use of the coupling assembly. Rather, the fluid connection is established by the end section of the tube fitted on the connector shaft. Moreover, no further components such as a sealing, or the like is required between the inner sleeve and the outer sleeve, or between the inner sleeve and the end section of the tube.

In a preferred embodiment, the interior surface of the second end section of the outer sleeve is provided with the protrusion extending in peripheral direction and the exterior surface of the inner sleeve is provided with the corresponding recess extending around at least a portion of an outer periphery of the inner sleeve. In an even more preferred embodiment, the protrusion may extend along an entire inner periphery of the outer sleeve on the outer sleeve's interior surface and/or the recess may extend around an entire outer periphery of the inner sleeve.

In some embodiments, the interior surface of the second end section of the outer sleeve is provided with a plurality of protrusions and the exterior surface of the inner sleeve is provided with a plurality of recesses, the plurality of protrusions configured to engage the plurality of recesses in a locking relationship. The plurality of protrusions may e.g. be arranged on the interior surface of the second end section of the outer sleeve in a sequence along an inner periphery of the interior surface of the second end section of the outer sleeve.

Similarly, the recesses may be arranged on the exterior surface of the inner sleeve along an outer periphery of the inner sleeve.

In an alternative embodiment, the interior surface of the second end section of the outer sleeve is provided with a recess e.g. extending in peripheral direction, and the exterior surface of the inner sleeve is provided with a protrusion e.g. extending around a portion of a periphery of the inner sleeve. The recess and the protrusion are configured to engage each other in a locking relationship. It is even more preferred that the recess extends around an entire inner periphery of the outer sleeve, and that the protrusion extends around an entire outer periphery of the inner sleeve. Alternatively, the interior surface of the second end section of the outer sleeve is provided with a plurality of recesses and the exterior surface of the inner sleeve is provided with a plurality of protrusions, the plurality of protrusions configured to engage the plurality of recesses in a locking relationship. The plurality of recesses may e.g. be arranged on the interior surface of the second end section of the outer sleeve in a sequence along an inner periphery of the second end section of the outer sleeve. Similarly, the protrusions may be arranged on the exterior surface of the inner sleeve along an outer periphery of the inner sleeve.

It is preferred that the plurality of protrusions and the plurality of recesses are arranged in a sequence along a peripheral direction to form a first ring of protrusions and a first ring of recesses, respectively. This results in a larger contact area between the inner sleeve and the outer sleeve and leads to an even more secure connection between them.

It is even more preferred that the interior surface of the second end section of the outer sleeve is provided with a second plurality of protrusions or a second plurality of recesses to engage a corresponding second plurality of recesses or a corresponding second plurality of protrusions on the exterior surface of the inner sleeve, wherein the second plurality of protrusions and the second plurality of recesses are arranged along a peripheral direction to form a second ring of protrusions and a second ring of recesses. The first ring of protrusions may be axially offset from the second ring of protrusions and the first ring of recesses may be axially offset from the second ring of recesses. In this, the axial directions and the peripheral directions are those defined by the inner sleeve or the outer sleeve, respectively, on which the protrusions or recesses are provided. Each of the protrusions may be sized and shaped to lockingly engage a corresponding recess.

Similarly, it is preferred that the protrusion(s) and the recess(es) extend in peripheral direction as this results in a larger contact area between the inner sleeve and the outer sleeve. In embodiments, in which the protrusion(s) and the recess(es) extend in peripheral direction, i.e. perpendicular to the correct pulling direction for disengagement, the engagement of the outer sleeve and the inner sleeve is thus more secure.

In a preferred embodiment, the outer sleeve is tapered, such that its cross-section at the first end thereof is smaller than its cross-section at the second end section thereof. When in use, the first end of the outer sleeve is directed away from the device and towards a distal end of the tube. As the outer sleeve is tapered, sharp edges are avoided, which could potentially damage the surrounding tissue. Moreover, forces acting upon the exterior surface of the outer sleeve are deflected to push the outer sleeve further onto the inner sleeve, thus resulting in an even more secure coupling.

In an alternative embodiment, the outer sleeve has a cylindrical shape. In this embodiment, an outer diameter and/or a cross-section of the outer sleeve at the first end of the outer sleeve equals an outer diameter or a cross-section at the second end section of the outer sleeve.

In a preferred embodiment, the inner sleeve is tapered, such that its cross-section at the first end thereof is smaller than its cross-section at the second end section thereof. When in use, the first end of the inner sleeve is directed away from the tube's end and the device. By providing the inner sleeve with a tapered shape, forces acting on the external surface of the inner sleeve will push the inner sleeve further towards the device, thus resulting in a more secure coupling between the tube and the connector shaft located within the inner sleeve.

It is, in particular, preferred that both the inner sleeve and the outer sleeve are tapered, such that their cross-section at the first ends is smaller than their cross-section at their second end sections.

In an alternative embodiment, the inner sleeve has a cylindrical shape. In this embodiment, an outer diameter and/or a cross-section of the inner sleeve at the first end of the inner sleeve equals an outer diameter or a cross-section at the second end section of the inner sleeve.

In a preferred embodiment, the inner sleeve has at least one slit extending from the second end of the inner sleeve and, in particular, extending along a longitudinal axis of the inner sleeve. The slit may extend over a portion of a length of the inner sleeve, preferably over at least a length of the second end section of the inner sleeve. The at least one slit may extend through an entire thickness of a wall of the inner sleeve. Providing slits is one way to provide the second end section of the inner sleeve with flexibility. This allows the inner sleeve to be easily pushed over the end section of the tube fitted on the connector shaft. When, in a subsequent step, the outer sleeve is pushed over the inner sleeve, the inner sleeve will be compressed, such that its cross-section at the second end section of the inner sleeve will become smaller, resulting in an even tighter engagement between the second end section of the inner sleeve, the end section of the tube and the connector shaft. In a preferred embodiment, the inner sleeve has at least one, in particular, at least two and, preferably, at least four slits extending from the second end of the inner sleeve and, in particular, extending along a longitudinal axis of the inner sleeve, preferably, for at least a length of the second end section of the inner sleeve.

According to a preferred embodiment, the outer sleeve has at least one slit extending from the second end of the outer sleeve and, in particular, extending along a longitudinal axis of the outer sleeve. The slit may extend over a portion of a length of the outer sleeve, preferably over at least a length of the second end section. The at least one slit may extend through an entire thickness of a wall of the outer sleeve. Similarly as described above for slits in the inner sleeve, this embodiment provides the outer sleeve with flexibility such that it may easily be pushed over the inner sleeve. In this, the protrusion provided on the interior surface of the second end section of the outer sleeve may easily slide over the exterior surface of the inner sleeve before engaging with the recess provided on the exterior surface of the inner sleeve. Similarly, in embodiments in which the inner surface of the second end section of the outer sleeve is provided with a recess, the second end section of the outer sleeve may easily slide over the exterior surface of the inner sleeve and over the protrusion provided thereon, until the protrusion on the exterior surface of the inner sleeve engages the recess in the interior surface of the outer sleeve. In an even more preferred embodiment, the outer sleeve has at least two, preferably at least four slits extending from the second end of the outer sleeve and, in particular, extending along a longitudinal axis of the outer sleeve, preferably, for at least a length of the second end section of the outer sleeve.

In embodiments in which the inner sleeve and/or the outer sleeve has at least one slit, the recess and/or protrusion may extend along an entire periphery of the inner sleeve and/or the outer sleeve, disrupted by the at least on slit. The slit or the slits extending over the length of the second end section of the outer sleeve or the inner sleeve may define one or more segments of the second end section of the inner sleeve or the outer sleeve between them. In some embodiments, each segment may be provided with a protrusion or a recess which, preferably, extends over an entire width of the segment in a peripheral direction.

For example, the outer sleeve may have N slits, defining N segments in the second end section of the outer sleeve. Each of the N segments may have a protrusion or recess on the interior surface thereof, preferably extending over an entire width of the segment. N may be an integer number of 1 or larger, in particular 2 or larger, and preferably 4.

Similarly, the inner sleeve may have M slits, defining M segments in the second end section of the inner sleeve. Each of the M segments may have a recess or a protrusion on the exterior surface thereof, preferably extending over an entire width of the segment. M may be an integer number of 1 or larger, in particular 2 or larger, and preferably 4.

According to a preferred embodiment, an interior surface of the second end section of the inner sleeve is provided with at least one internal lip. The internal lips may be adapted to engage a corresponding flange provided on the external surface of a connector shaft of the device. In use, the second end section of the inner sleeve may be pushed onto the end of the tube fitted on the connector shaft until the lip on the interior surface of the second end section of the inner sleeve is pushed beyond the flange of the connector shaft, thus preventing that the inner sleeve is pulled off the connector shaft and the end section of the tube.

The at least one internal lip may be directed inwardly. In some embodiments, the at least one lip may have a surface that is tapered towards the second end of the inner sleeve to facilitate pushing the lip over the flange of the connector shaft. The at least one lip may e.g. be angled towards the second end of the inner sleeve.

In some embodiments, an interior surface of the second end section of the inner sleeve is provided with a plurality of internal lips. For example, in embodiments, in which the inner sleeve comprises one or more slits defining one or more segments in the second end section of the inner sleeve between them, each of the segments may be provided with an internal lip, in particular, extending over an entire width of the segment in peripheral direction.

In a preferred embodiment, the at least one internal lip on the internal surface of the second end section of the inner sleeve extends along a peripheral direction of the inner sleeve. This results in a larger contact line between the internal lip on the inner sleeve and a corresponding flange on the connector shaft. It is even more preferred that the internal lip on the interior surface of the second end section of the inner sleeve extends along an entire inner periphery of the inner sleeve, possibly disrupted by one or more slits in the inner sleeve.

The at least one internal lip may be provided on the interior surface of the inner sleeve at a same position as the recess or protrusion that is provided on the exterior surface of the inner sleeve. In other words, the internal lip and the recess or protrusion may be at a same position on opposite sides of a wall of the inner sleeve.

According to a preferred embodiment, the inner sleeve and/or the outer sleeve has a cylindrical, a conical or a truncated-conical shape. A cross section of the inner sleeve and/or the outer sleeve may be circular.

In some embodiments, the inner sleeve and/or the outer sleeve comprises an elastic material. For example, the inner sleeve and/or the outer sleeve may consist of an elastic plastic material, such as a biocompatible plastic material. In other embodiments, the inner sleeve and/or the outer sleeve may comprise a sheet metal, such as a biocompatible sheet metal, e.g. a biocompatible sheet metal alloy. As previously mentioned, the second end section of the inner sleeve may e.g. be flexible since the second end section comprises an elastic material and/or due to one or more slits provided in the second end section of the inner sleeve. Similarly, the second end section of the outer sleeve may in some embodiments be flexible e.g. due to the second end section comprising an elastic material and/or due to one or more slits provided in the second end section of the outer sleeve.

In a further aspect, a kit is provided, comprising a first tube, a device having a first connector shaft, and a first coupling assembly of the aforementioned type. An end section of the first tube is sized and configured to fit on the first connector shaft, and the second end section of the inner sleeve of the first coupling assembly is sized and configured to surround and engage the end section of the first tube fitted on the first connector shaft, thereby clamping the end section of the first tube between the first connector shaft and the second end section of the inner sleeve.

An inner cross section of the end section of the first tube may be sized and shaped to tightly, and in particular elastically, fit on the first connector shaft. The fitting of the end section of the tube on the connector shaft may form a fluid-tight seal. The end section of the first tube may e.g. comprise a flexible material, such as a plastic material, e.g. a biocompatible plastic material. This allows the end section of the tube to elastically expand when pushed over the connector shaft. When assembled, the end section of the tube may tightly fit on the connector shaft and may be held in place by elastic forces of the tube material. The coupling assembly of the invention may be used to further secure the coupling between the end section of the tube and the connector shaft. Yet, it should be understood that the coupling assembly may also be used to secure the tube to the connecting shaft in embodiments in which the end section of the tube is not elastic.

In the assembled state, the end section of the first tube may be in direct contact with the first connector shaft. In some embodiments, a seal, such as an annular seal, may be arranged between the first connector shaft and the end section of the first tube.

The first connector shaft may comprise a plastic material, such as a biocompatible plastic material, or a metal, such as a biocompatible metal. The first connector shaft may in some embodiments comprise an elastic material, though not limited in this regard. The device and/or the first tube may be adapted to be implanted into a body of a patient, such as a human or an animal.

The first connector shaft may define a first channel therein that is connected to a first opening in a distal end thereof. The first channel may e.g. be in fluid communication with a valve, a filter and/or a pump of the device.

In a preferred embodiment, the first connector shaft has a distal end and an opposite proximal end, the proximal end of the first connector shaft connected to a body of the device. In this embodiment, an exterior surface of the first connector shaft at its distal end has an external flange extending along at least a portion of a periphery of the first connector shaft, and the interior surface of the second end section of the inner sleeve of the first coupling assembly has at least one internal lip configured to engage the external flange of the first connector shaft.

In this embodiment, the inner sleeve of the coupling assembly may easily by pushed over the end section of the tube fitted on the connector shaft until the at least one internal lip is located beyond the external flange, i.e. between the distal end and the proximal end of the connector shaft. When assembled, the external flange and the at least one internal lip may form a form fit, which prevents the inner sleeve from sliding off the connector shaft. In particular, the at least one internal lip may be configured to snap on the connector shaft between the distal end and the proximal end thereof due to the flexibility of the second end section of the inner sleeve. In an assembled state, the inner sleeve may therefore be held on the connector shaft by a locking engagement between the at least one lip and the external flange. Preferably, the external flange extends along an entire outer periphery of the first connector shaft.

The first connector shaft being connected to the body of the device does not necessarily imply that these are provided as separate pieces. In some embodiments, the connecting shaft and the body or at least a housing of the device may be provided as a single, unitary piece.

In some embodiments, a distance between the external flange at the distal end of the first connector shaft and the proximal end of the first connector shaft may be larger than a distance between the internal lip on the interior surface of the inner sleeve of the first coupling assembly and the second end of the inner sleeve of the first coupling assembly.

In some embodiments, the external flange and/or the at least one internal lip may be tapered to facilitate pushing the inner sleeve onto the connector shaft. The flange may e.g. be tapered in a direction away from the proximal end of the connecting shaft, e.g. it may be tapered such that it has a larger cross section or outer diameter on a side facing the proximal end of the connector shaft than on an opposite side facing away from the proximal end of the connector shaft. The at least one lip may be tapered towards the second end of the inner sleeve.

In a preferred embodiment, the device comprises a housing. The housing may be waterproof and/or may on its exterior consist of a biocompatible material, such as a polymer or a metal. According to a preferred embodiment, the device further comprises a second connector shaft, and the kit further comprises a second tube and a second coupling assembly of the aforementioned type. In this embodiment, an end section of the second tube is sized and configured to fit on the second connector shaft, and the second end section of the inner sleeve of the second coupling assembly is sized and configured to surround and engage the end section of the second tube fitted on the second connector shaft, thereby clamping the end section of the second tube between the second connector shaft and the second end section of the inner sleeve.

The second connector shaft and the second coupling assembly may further include features that have been described above with respect to the first connector shaft and the first coupling assembly, and which are thus not repeated here. In some embodiments, the first and second connector shafts may be identical and/or the first and second coupling assemblies may be identical.

The first and second connector shafts may be located on different sides of a housing of the device. For example, the first and second connector shafts may be located on opposite sides of the housing.

In a preferred embodiment, the second connector shaft has a distal end and an opposite proximal end, the proximal end of the second connector shaft connected to the body of the device, wherein an exterior surface of the second connector shaft at its distal end has an external flange extending along at least a portion of a periphery of the second connector shaft, and wherein the interior surface of the second end section of the inner sleeve of the second coupling assembly has at least one internal lip configured to engage the external flange of the second connector shaft.

As previously described with respect to the first connector shaft and the first coupling assembly, when assembled, the external flange and the at least one internal lip may form a form fit, which prevents the inner sleeve from sliding off the connector shaft. In an assembled state, the inner sleeve may therefore be held on the connector shaft by a locking engagement between the at least one lip and the external flange. Preferably, the external flange extends along an entire periphery of the second connector shaft.

In a further aspect, a method for securing an end section of a tube to a connector shaft of a device is provided. The method comprises mounting a coupling assembly of the aforementioned type on the tube, the inner sleeve of the coupling assembly closer to the end section of the tube than the outer sleeve of the coupling assembly, and the second ends of the inner sleeve and the outer sleeve directed towards the end section of the tube. The method further comprises fitting the end section of the tube over the connector shaft, and pushing the second end section of the inner sleeve of the coupling assembly over the end section of the tube fitted over the connector shaft. The method further comprises pushing the second end section of the outer sleeve of the coupling assembly over the inner sleeve, until the protrusion and the recess on the interior surface of the second end section of the outer sleeve and on the exterior surface of the inner sleeve, respectively, engage in a locking relationship.

In some embodiments, the method steps are carried out in the order given above. Yet, in some embodiments, the end section of the tube may first be fitted on the connecting shaft before the coupling assembly is mounted on the tube from the tube's opposite free end. The skilled person will further understand that the above method steps may be repeated for a kit having a second tube, a second coupling assembly and a device having a second connector shaft.

BRIEF DESCRIPTION OF THE DRAWINGS

Further features and advantages of the present invention will become evident to the skilled person when reading the following detailed description in conjunction with the provided drawings, in which like reference numerals are used to denote like elements, and in which.

DETAILED DESCRIPTION OF THE INVENTION

Figure 1:
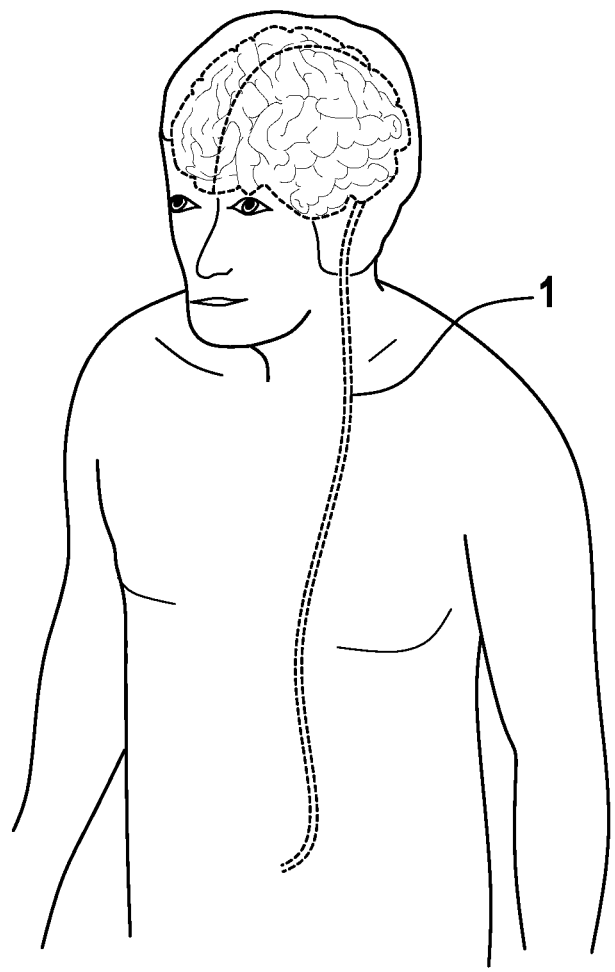
FIG. 1 shows a 3D diagram of a patient having implanted a catheter assembly.
Figure 2:
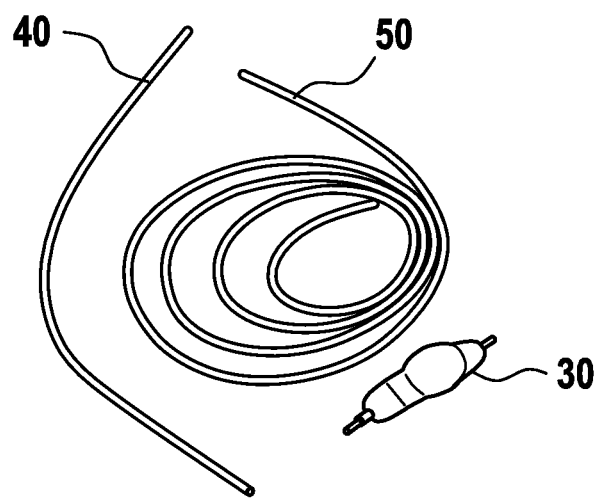
FIG. 2 shows a kit according to an embodiment in the unassembled state.

FIG. 2 shows a kit according to an embodiment of the invention. The kit shown in FIG. 2 is in the form of a catheter kit, which may be used to transfer excess CSF from the brain to another part of the patient's body, such as the peritoneal cavity. The kit comprises a first tube 40, which in this embodiment is a ventricular catheter tube, and a second tube 50, which in this embodiment is a distal catheter tube. The kit further comprises a device 30, which includes a housing and a valve located inside the housing. Yet, in other embodiments, the device may alternatively or additionally include other elements, such as a filter and/or a pump.

Figure 3:
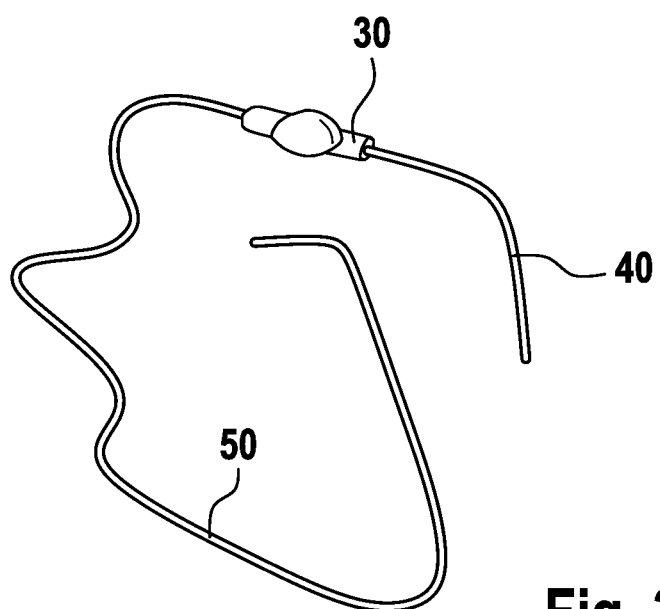
FIG. 3 shows the kit of FIG. 2 in the assembled state.

While FIG. 2 shows the kit in the unassembled state, FIG. 3 shows the same kit in the assembled state. As can be seen from FIG. 3, one end section of the ventricular catheter tube 40 is connected to the device 30. To this effect, an inner diameter or cross section of an end section of the tube 40 may be sized and shaped to tightly fit over a first connector shaft (not shown) of the device 30. Moreover, one end section of the distal catheter tube 50 is also connected to the device 30. To this effect, an inner diameter or cross section of an end section of the tube 50 may be sized and shaped to tightly fit over a second connector shaft (not shown) of the device 30. The connector shafts are provided on opposite sides of the housing of device 30. To assemble the kit of FIG. 2, one end section of the ventricular catheter tube 40 is fitted over the first connector shaft of the device 30. Similarly, one end section of the distal catheter tube 50 is fitted over the second connector shaft of the device 30. To secure the connection between each catheter tube 40, 50 and the respective connector shaft, a respective coupling assembly is used, which will now be described in more details with reference to FIG. 4.

Figure 4:
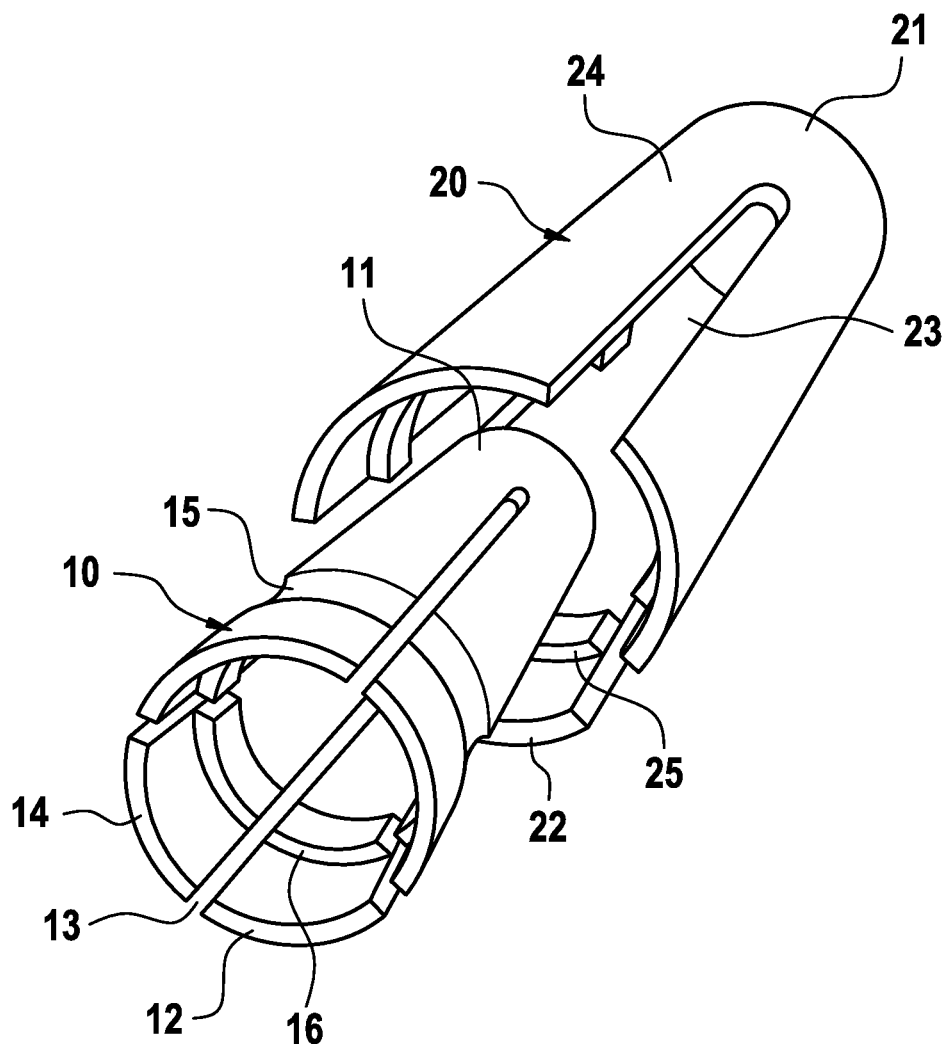
FIG. 4 shows a perspective view of a coupling assembly according to an embodiment.

FIG. 4 shows a perspective view of a coupling assembly according to an embodiment. The coupling assembly comprises an inner sleeve 10 and an outer sleeve 20. The inner sleeve 10 comprises a first end 11 and an opposite second end 12. The inner sleeve 10 is tapered from its second end to its first end, such that the inner sleeve 10 has a larger cross-section and diameter at its second end 12 than at its first end 11. The inner sleeve 10 defines a longitudinal axis. The inner sleeve 10 further has defined therein slits 13 which extend from the second end 12 of the inner sleeve 10 along the inner sleeve's 10 longitudinal axis over a portion of the inner sleeve's 10 length which corresponds to a second end section of the inner sleeve 10. A plurality of segments 14 is defined between the slits 13.

By virtue of the slits 13, the inner sleeve 10 is provided with flexibility at its second end 12, such that the segments 14 may be elastically deflected outwardly in a radial direction with respect to the inner sleeve 10. On an interior surface of the inner sleeve 10 close to the inner sleeve's 10 second end 12, a plurality of lips 16 is provided. In the embodiment of FIG. 4, each segment 14 is provided with a lip 16 on its interior surface. The lips 16 extend in a peripheral direction and are directed inwardly. The lips 16 are configured to engage a corresponding flange provided on a connector shaft of a device, as will be described in more detail below with respect to FIGS. 5 and 6.

The coupling assembly further comprises an outer sleeve 20. The outer sleeve 20 has a first end 21 and an opposite second end 22. The outer sleeve 20 is tapered from its second end 22 to its first end 21, such that the outer sleeve 20 has a larger cross-section and diameter at its second end 22 than at its first end 21. Moreover, the outer sleeve 20 is provided with a plurality of slits 23, which extend from the outer sleeve's 20 second end 22 along a longitudinal axis of the outer sleeve 20 for a portion of the outer sleeve's 20 length that corresponds to a second end section of the outer sleeve 20. An inner diameter of the outer sleeve 20 at its second end 22 is sized and shaped to receive the first end 11 of the inner sleeve 10. This way, at least a portion of the outer sleeve 20 may be pushed over the inner sleeve 10.

Between the slits 23 in the outer sleeve 20, a plurality of segments 24 is defined. On the interior surface of the outer sleeve 20, a plurality of protrusions 25 is provided. Each segment 24 is provided with a protrusion 25 on the interior surface thereof. The protrusions 25 extend in a peripheral direction, i.e. perpendicular to the outer sleeve's 20 longitudinal axis. The exterior surface of the inner sleeve 10 is provided with a plurality of corresponding recesses 15. The recesses are located on the segments 14 of the inner sleeve 10. Each segment 14 is provided with a recess 15 on the exterior surface thereof. The recesses 15 are in the form of grooves and extend in a peripheral direction around the longitudinal axis of the inner sleeve. The recesses 15 are located at about the same position as the lips 16 discussed above, yet on an opposite side of the inner sleeve's wall.

When the second end 22 of the outer sleeve 20 is pushed over the first end 11 of the inner sleeve, the protrusions 25 on the interior surface of the outer sleeve 20 will first contact the exterior surface of the inner sleeve 10. As the inner sleeve 10 is tapered, an increasing force will be applied to the protrusions 25 on the interior surface of the outer sleeve 20 when further pushing the outer sleeve 20 over the inner sleeve 10, which force is directed radially outwardly. As the outer sleeve 20 is provided with flexibility at its second end 22 due to the slits 23, the segments 24 are deflected radially outwardly, such that the cross-section of the outer sleeve 20 at its second end 22 increases. This way, the second end 22 of the outer sleeve 20 may easily slide over the exterior surface of the inner sleeve 10. When the protrusions 25 on the interior surface of the outer sleeve 20 reach the recesses 15 on the exterior surface of the inner sleeve 10, the protrusions 25 and the recesses 15 engage. In this, the protrusions 25 snap into the recesses 15 by virtue of the elastic force due to the segments 24. This elastic force was previously generated by deflecting the segments 24 of the outer sleeve 20 outwardly. The protrusions 25 and the recesses 15 provide a locking engagement between the outer sleeve 20 and the inner sleeve 10.

Figure 5:
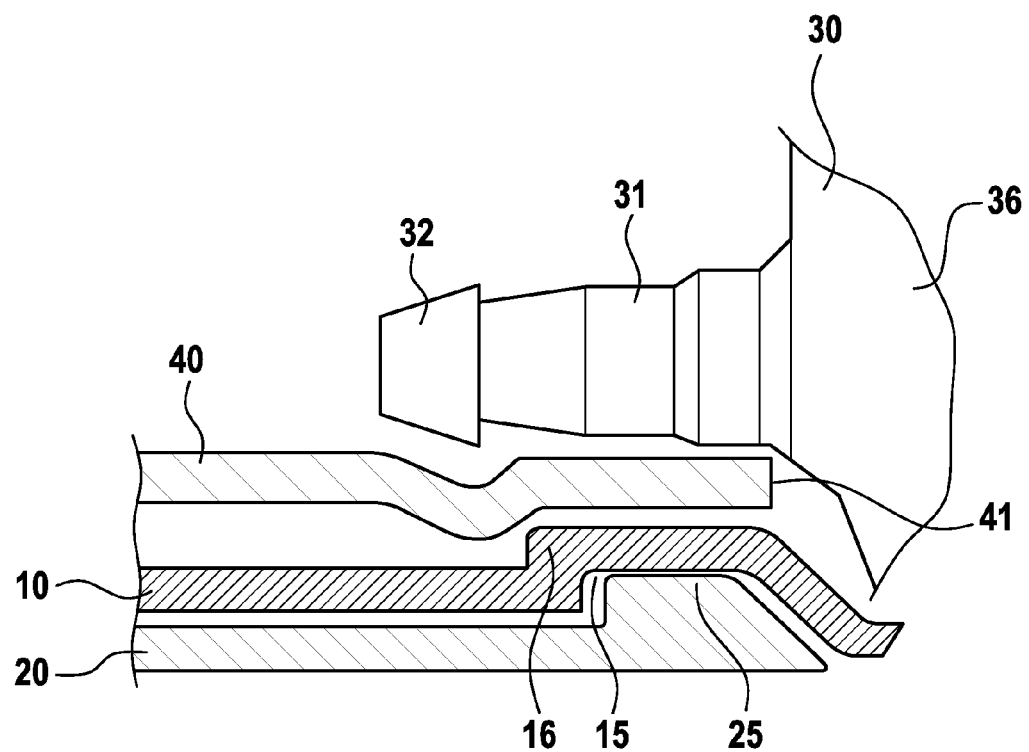
FIG. 5 shows a part of a schematic cross-section through a kit comprising a device having a connector shaft, a tube and a coupling assembly according to an embodiment.

FIG. 5 shows a schematic cross-section through a part of a coupling assembly mounted on a device 30. The device 30 has a connector shaft 31 connected to a body 36. The body may e.g. house a filter, a valve and/or a pump. An end section 41 of a tube 40 is fitted over the connector shaft 31 to provide a fluid connection between the tube 40 and a channel in the connector shaft 31. The coupling assembly comprising an inner sleeve 10 and an outer sleeve 20 is mounted over the tube 40 and the connector shaft 31. As the coupling assembly is provided on the outside of the tube, it does not get into contact with the fluid passing through the tube 40 and the connector shaft 31. Hence, there is no interaction between the fluid and the inner sleeve 10 or the outer sleeve 20. At its distal end, the connector shaft 31 is provided with an external flange 32. The tube's end section 41 is elastic, such that it fits over the connector shaft 31 and the flange 32 at its distal end.

To assemble the kit shown in FIG. 5, first, the outer sleeve 20 and the inner sleeve 10 are loosely mounted over the tube 40, such that the second ends 12, 22 of the inner sleeve 10 and the outer sleeve 20 are directed towards the tube's end section 41, which is to be fitted on the connector shaft 31. The inner sleeve 10 and the outer sleeve 20 are orientated such that the inner sleeve 10 is closer to the tube's end section 41 than the outer sleeve 20. The inner sleeve 10 and the outer sleeve 20 surround the tube 40. The end section 41 of the tube 40 is then pushed over the connector shaft 31. As the end section 41 is elastic, it easily expands, resulting in a tight and sealing fit with the connector shaft 31.

Next, the inner sleeve 10 is pushed over the end section 41 of the tube 40 fitted on the connecting shaft 31. When the lips 16 reach the position of the flange 32 of the connector shaft 31, they experience a force that is directed radially outwardly. Due to the force, the segments 14 of the inner sleeve 10 will be elastically deflected outwardly. The lips 16 can thus pass over the flange 32 with the end section 41 of the tube 40 still arranged between the flange 32 and the lips 16. When the lips 16 have slid past the flange 32, the lips 16 and the flange 32 provide a form fit, securing the inner sleeve 10 to the connector shaft 31 and clamping the end section 41 of the tube 40 between them.

To facilitate sliding the lips 16 over the flange 32, the flange 32 is tapered, such that its outer diameter further away from the device body 36 is smaller than an outer diameter of the flange 32 closer to the body 36. Similarly, the lips 16 on the interior surface of the inner sleeve 10 are tapered towards the second end 12 of the inner sleeve 10.

In a next step, the second end 22 of the outer sleeve 20 is pushed over the first end 11 of the inner sleeve 10, until the protrusions 25 provided on the interior surface of the outer sleeve 20 reach the recesses 15 provided on the exterior surface of the inner sleeve 10. As explained above, the segments 24 of the outer sleeve 20 are deflected outwardly when the outer sleeve 20 is pushed over the inner sleeve 10. As soon as the protrusions 25 reach the position of the recesses 15, the protrusions 25 are pushed into the recesses 15 by the elastic force exerted by the segments 24, providing a locking engagement of the protrusions 25 and the recesses 15. In this assembled state, the coupling assembly is fully mounted, securing the coupling between the end section 41 of the tube 40 and the connector shaft 31.

Figure 6:
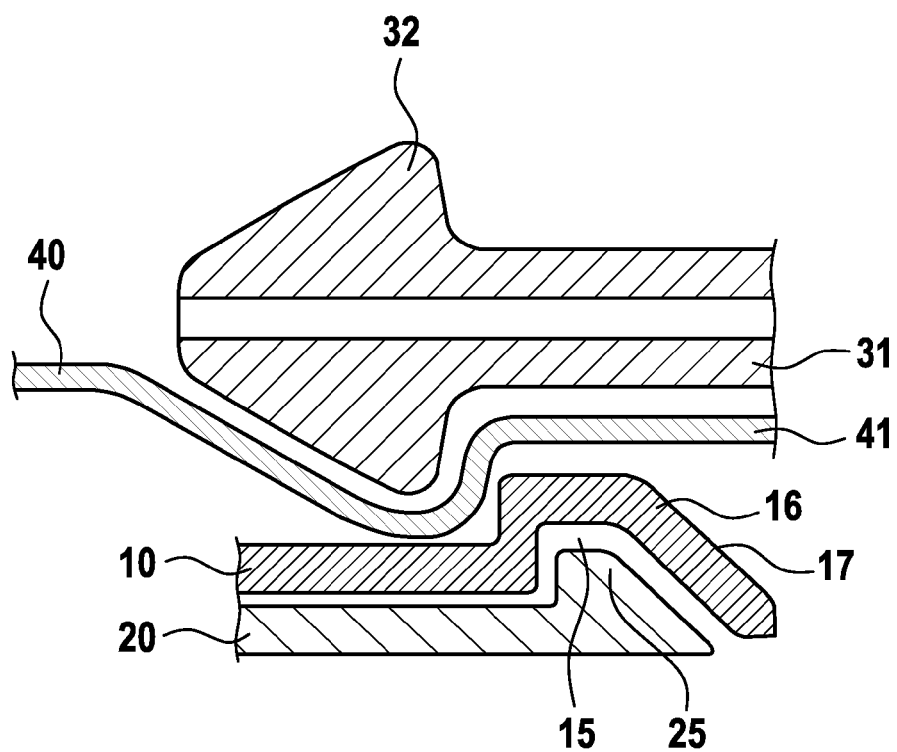
FIG. 6 shows a part of another schematic cross-section through a kit according to an embodiment.

FIG. 6 shows a cross-section through a portion of the kit according to an embodiment in greater detail. As can be seen from FIG. 6, the end section 41 of the tube 40 is fitted over the connector shaft 31. The lips 16 on the interior surface of the inner sleeve 10 are lockingly engaged with the flange 32 provided on the distal end of the connector shaft 31. The flange 32 and the connector shaft 31 are tapered, such that an outer diameter of the flange 32 at the distal end of the connector shaft 31 is smaller than an outer diameter of the flange 32 closer to the body of the device. Similarly, each lip 16 is provided with a surface section 17 tapered towards the second end 12 of the inner sleeve 10.

The outer sleeve 20 is pushed over the inner sleeve 10, such that the protrusions 25 provided on the interior surface of the outer sleeve 20 engage with the recesses 15 provided on the exterior surface of the inner sleeve 10. FIG. 6 illustrates the assembled state of the kit.

Figure 7:
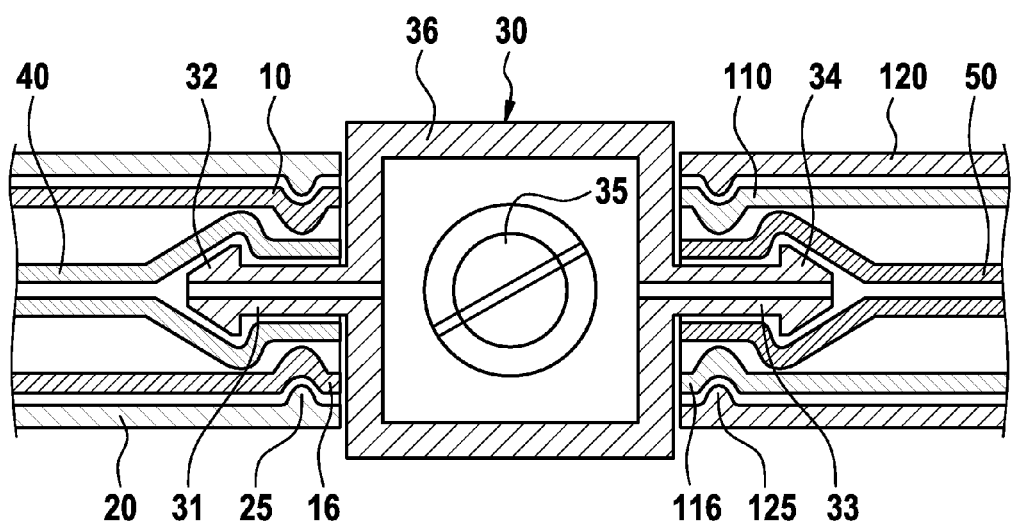
FIG. 7 shows a schematic cross-section through a kit according to an embodiment, in which the device has two connector shafts.

FIG. 7 shows a schematic cross-section through a kit according to an embodiment, in the form of a catheter kit. The kit of FIG. 7 comprises a device 30 with two connector shafts 31, 33. Each connector shaft 31, 33 is provided with an external flange 32, 34 at a distal end thereof. Moreover, the proximal ends of the connector shafts 31, 33 are connected to a body 36 of the device 30. As schematically shown in FIG. 7, the device 30 may contain a valve 35. In other embodiments, the device 30 may additionally or alternatively contain a filter and/or a pump.

Over each connector shaft 31, 33, an end section of a respective tube 40, 50 is fitted. As described above, the end sections of the tubes 40, 50 are elastic, such that they are held on the connector shafts 31, 33 by elastic force. Yet, to secure the coupling between the tubes 40, 50 and the respective connector shafts 31, 33, two coupling assemblies are used. The method for securing tube 40 to connector shaft 31, using inner sleeve 10 and outer sleeve 20, on the left hand side of FIG. 7 is the same as previously described with respect to FIGS. 5 and 6. An identical assembly is provided on the right hand side of FIG. 7 to secure the tube 50 to the connector shaft 33 of the device 30. In this, an inner sleeve 110 having lips 116 provided on the interior surface thereof is used. Moreover, an outer sleeve 120 having protrusions 150 on the interior surface thereof is mounted over the inner sleeve 110. As the features and the use of the coupling assembly used on the right hand side of FIG. 7 to secure the tube 50 to the connector shaft 33 are identical to the ones previously described with respect to inner sleeve 10 and outer sleeve 20 in FIGS. 5 and 6, repetition is avoided here.

Figure 8:
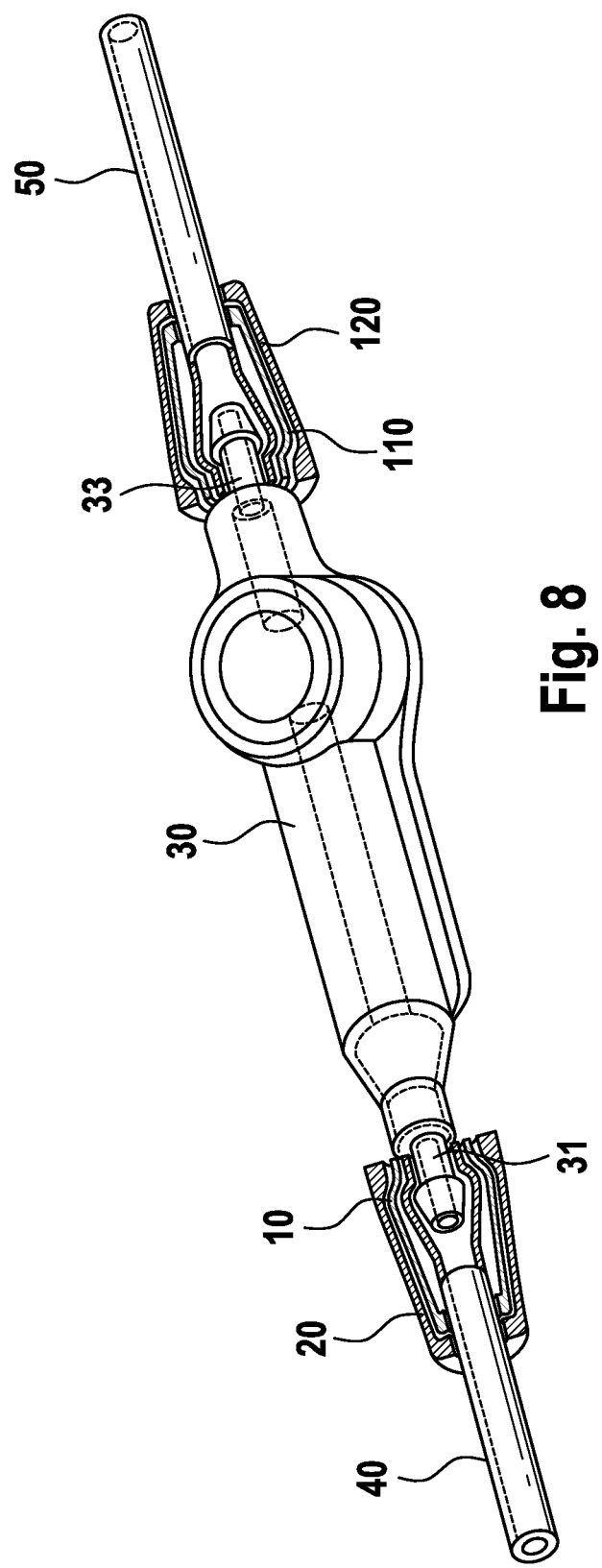
FIG. 8 shows a perspective view of a kit according to an embodiment.

FIG. 8 shows a perspective view of a kit according to an embodiment, forming a catheter kit. The kit comprises a device 30, which may contain a valve. Moreover, the kit comprises a first tube 40 which is fitted over a first connector shaft 31 of the device 30. Moreover, the kit comprises a second tube 50 which is fitted over a second connector shaft 33 of the device 30. To secure the first tube 40 to the first connector shaft 31, a first coupling assembly comprising inner sleeve 10 and outer sleeve 20 is used. Similarly, to secure the second tube 50 to the second connecting shaft 33, a second coupling assembly comprising inner sleeve 110 and outer sleeve 120 is used.

Figure 9:
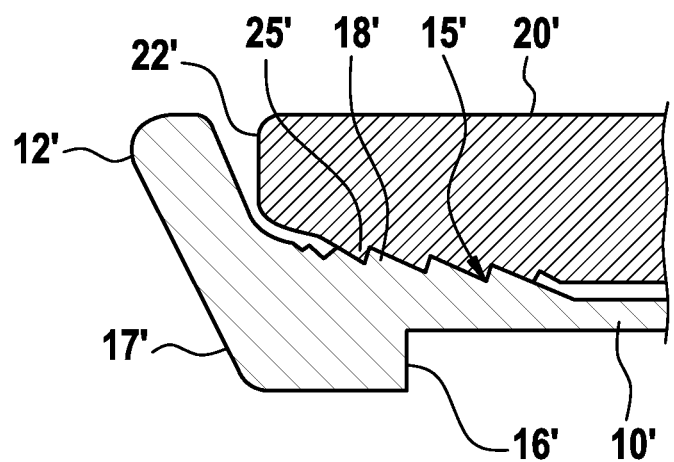
FIG. 9 shows a part of a schematic cross-section through a coupling assembly according to an embodiment.

FIG. 9 shows a schematic cross section through a part of a coupling assembly according to an alternative embodiment, in the assembled state. The coupling assembly is similar to the one discussed above, such that only the differences will be highlighted, to avoid repetition. The coupling assembly of FIG. 9 includes a plurality of recesses and protrusions on the inner and outer sleeve that are offset in axial direction. In more detail, the coupling assembly comprises an inner sleeve 10' having a second end 12'. The exterior surface of the inner sleeve 10' has a lip 16' extending around a periphery of the inner sleeve 10' to engage a flange provided on a connector shaft of a device (not shown in FIG. 9). Moreover, a tapered surface section 17' is provided at the second end 12' of the inner sleeve 10' to facilitate sliding the inner sleeve 10' over the flange provided on a connector shaft. The tapered surface section 17' is located between the second end 12' and the lip 16'. Moreover, a plurality of teeth 18' is provided on the exterior surface of the inner sleeve 10'. The teeth 18' are arranged in rings extending along an outer periphery of the inner sleeve 10'. The inner sleeve 10' includes a plurality of such rings. A plurality of recesses 15' is defined between each two adjacent rings of teeth 18'. Accordingly, the recesses 15' extend along an outer periphery of the inner sleeve 10' and are arranged in a plurality of rings, which rings are axially offset with respect to each other along an axial axis defined by the inner sleeve 10'.

The coupling assembly further comprises an outer sleeve 20' having a second end 22'. On the interior surface of the outer sleeve 20', a plurality of tooth-like protrusions 25' is formed. The protrusions 25' are arranged in rings extending along the inner periphery of the outer sleeve 20'. The rings are axially offset with respect to each other along an axial axis defined by the outer sleeve 20'. The protrusions 25' are sized and shaped to engage the recesses 15' provided on the exterior surface of the inner sleeve 10'.

Modifications of the embodiments described above are possible and will be readily recognized by the skilled person. For example, the coupling assembly or the kit may in some embodiments be useable for other medical or non-medical purposes. The coupling assembly or the kit may be located inside or outside a patient's body. The inner and/or outer sleeves may entirely or partially consist of an elastic material. In some embodiments, the inner sleeve and/or the outer sleeve may have a cylindrical shape, such that their outer diameter or cross-section and the first end thereof equal their outer diameter or cross-section and the second end thereof, respectively.

The invention claimed is:

1. A coupling assembly comprising:
   an inner sleeve having a first end, an opposite second end, a first end section at the first end of the inner sleeve and a second end section at the second end of the inner sleeve;
   an outer sleeve having a first end, an opposite second end and a second end section at the second end of the outer sleeve,
   wherein the outer sleeve has at least one slit extending from the second end of the outer sleeve,
   wherein the second end section of the outer sleeve is sized and shaped to receive at least the first end section of the inner sleeve therein,
   wherein an interior surface of the second end section of the outer sleeve is provided with a protrusion to engage a corresponding recess on an exterior surface of the inner sleeve,
   wherein at least one inwardly directed lip is provided on an interior surface of the inner sleeve close to the inner sleeve's second end, said at least one inwardly directed lip being configured to engage a corresponding flange provided on a connector shaft of a device,
   wherein the recess on the exterior surface of the inner sleeve is located at the same position as the at least one inwardly directed lip, yet on an opposite side of a wall of the inner sleeve, and
   wherein the second end section of the inner sleeve is flexible.

2. The coupling assembly of claim 1,
   wherein the protrusion at the interior surface of the second end section of the outer sleeve extends in a peripheral direction, and
   wherein the recess at the exterior surface of the inner sleeve extends around at least a portion of a periphery of the inner sleeve.

3. The coupling assembly of claim 1, wherein the protrusion at the interior surface of the second end section of the outer sleeve includes a plurality of protrusions to engage a corresponding plurality of recesses of the recess on the exterior surface of the inner sleeve.

4. The coupling assembly of claim 1,
   wherein the protrusion at the interior surface of the second end section of the outer sleeve includes a plurality of protrusions to engage a corresponding plurality of recesses of the recess on the exterior surface of the inner sleeve, and
   wherein the plurality of protrusions and the plurality of recesses are arranged in a sequence along a peripheral direction, to form a first ring of protrusions and a first ring of recesses, respectively.

5. The coupling assembly of claim 1,
   wherein the protrusion at the interior surface of the second end section of the outer sleeve includes a plurality of protrusions to engage a corresponding plurality of recesses of the recess on the exterior surface of the inner sleeve,
   wherein the plurality of protrusions and the plurality of recesses are arranged in a sequence along a peripheral direction, to form a first ring of protrusions and a first ring of recesses, respectively,
   wherein the interior surface of the second end section of the outer sleeve is provided with a second plurality of protrusions to engage a corresponding second plurality of recesses on the exterior surface of the inner sleeve, and
   wherein the second plurality of protrusions and the second plurality of recesses are arranged along said peripheral direction to form a second ring of protrusions and a second ring of recesses.

6. The coupling assembly of claim 1, wherein the outer sleeve is tapered, such that its cross section at the first end thereof is smaller than its cross section at the second end section thereof.

7. The coupling assembly of claim 1, wherein the outer sleeve has a cylindrical shape.

8. The coupling assembly of claim 1, wherein the inner sleeve is tapered, such that its cross section at the first end thereof is smaller than its cross section at the second end section thereof.

9. The coupling assembly of claim 1, wherein the inner sleeve has a cylindrical shape.

10. The coupling assembly of claim 1, wherein the inner sleeve has at least one slit extending from the second end of the inner sleeve.

11. The coupling assembly of claim 1, wherein the at least one inwardly directed lip extends in a peripheral direction of the inner sleeve.

12. The coupling assembly of claim 1, wherein at least one of the second end section of the inner sleeve and the second end section of the outer sleeve comprises an elastic material.

13. A kit, comprising
    a first tube,
    a device having a first connector shaft and a first coupling assembly according to claim 1,
    wherein an end section of the first tube is sized and configured to fit on the first connector shaft, and
    wherein the second end section of the inner sleeve of the first coupling assembly is sized and configured to surround and engage the end section of the first tube fitted on the first connector shaft, thereby clamping the end section of the first tube between the first connector shaft and the second end section of the inner sleeve.

14. The kit of claim 13,
    wherein the first connector shaft has a distal end and an opposite proximal end, the proximal end of the first connector shaft connected to a body of the device, wherein an exterior surface of the first connector shaft at its distal end has an external flange extending along at least a portion of a periphery of the first connector shaft, and wherein the at least one inwardly directed lip of the first coupling assembly is configured to engage the external flange of the first connector shaft.

15. The kit of claim 13,
wherein the device further comprises a second connector shaft,
wherein the kit further comprises a second tube and a second coupling assembly according to claim 1,
wherein an end section of the second tube is sized and configured to fit on the second connector shaft, and
wherein the second end section of the inner sleeve of the second coupling assembly is sized and configured to surround and engage the end section of the second tube fitted on the second connector shaft, thereby clamping the end section of the second tube between the second connector shaft and the second end section of the inner sleeve.

16. The kit of claim 15,
wherein the second connector shaft has a distal end and an opposite proximal end, the proximal end of the second connector shaft connected to a body of the device,
wherein an exterior surface of the second connector shaft at its distal end has an external flange extending along at least a portion of a periphery of the second connector shaft.

17. A method for securing an end section of a tube to a connector shaft of a device, the method comprising:
mounting a coupling assembly according to claim 1 on the tube, the inner sleeve of the coupling assembly closer to the end section of the tube than the outer sleeve of the coupling assembly, and the second ends of the inner sleeve and the outer sleeve directed towards the end section of the tube,
fitting the end section of the tube over the connector shaft,
pushing the second end section of the inner sleeve of the coupling assembly over the end section of the tube fitted over the connector shaft, and
pushing the second end section of the outer sleeve of the coupling assembly over the inner sleeve, until the protrusion and the recess on the interior surface of the second end section of the outer sleeve and on the exterior surface of the inner sleeve, respectively, engage in a locking relationship.

18. A kit, comprising
a first tube;
a second tube;
a device having a first connector shaft and a second connector shaft; and
a first and a second coupling assembly, wherein each coupling assembly comprises:
an inner sleeve having a first end, an opposite second end, a first end section at the first end of the inner sleeve and a second end section at the second end of the inner sleeve,
an outer sleeve having a first end, an opposite second end and a second end section at the second end of the outer sleeve,
wherein the second end section of the outer sleeve is sized and shaped to receive at least the first end section of the inner sleeve therein,
wherein an interior surface of the second end section of the outer sleeve is provided with a protrusion or a recess to engage a corresponding recess or protrusion on an exterior surface of the inner sleeve, and
wherein the second end section of the inner sleeve is flexible;
wherein an end section of the first tube is sized and configured to fit on the first connector shaft;
wherein the second end section of the inner sleeve of the first coupling assembly is sized and configured to surround and engage the end section of the first tube fitted on the first connector shaft, thereby clamping the end section of the first tube between the first connector shaft and the second end section of the inner sleeve;
wherein an end section of the second tube is sized and configured to fit on the second connector shaft;
wherein the second end section of the inner sleeve of the second coupling assembly is sized and configured to surround and engage the end section of the second tube fitted on the second connector shaft, thereby clamping the end section of the second tube between the second connector shaft and the second end section of the inner sleeve;
wherein the first connector shaft defines a first channel therein that is connected to a first opening in a distal end thereof, and the second connector shaft defines a second channel therein that is connected to a second opening in a distal end thereof,
wherein the first and second channels are in fluid communication with each other, or are in fluid communication with a valve, a filter or a pump of the device.

* * * * *